(12) United States Patent
Schnee

(10) Patent No.: US 8,435,797 B2
(45) Date of Patent: May 7, 2013

(54) ELECTROLUMINESCENT DIODE SENSOR

(75) Inventor: Vincent P. Schnee, Alexandria, VA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 325 days.

(21) Appl. No.: 12/961,675

(22) Filed: Dec. 7, 2010

(65) Prior Publication Data

US 2012/0142112 A1   Jun. 7, 2012

(51) Int. Cl.
*G01N 33/22* (2006.01)
*G01N 21/66* (2006.01)

(52) U.S. Cl.
USPC ............... 436/107; 422/82.05; 422/82.08; 436/106; 436/110; 436/172

(58) Field of Classification Search .......... 436/110, 436/172, 106–107; 422/82.05, 82.08
See application file for complete search history.

(56) References Cited

U.S. PATENT DOCUMENTS

| | | | | |
|---|---|---|---|---|
| 5,334,539 | A * | 8/1994 | Shinar et al. | 438/22 |
| 5,352,906 | A * | 10/1994 | Shinar et al. | 257/40 |
| 5,821,567 | A | 10/1998 | Ogihara et al. | |
| 6,136,627 | A | 10/2000 | Ogihara et al. | |
| 6,267,913 | B1 * | 7/2001 | Marder et al. | 252/582 |
| 6,331,438 | B1 * | 12/2001 | Aylott et al. | 436/172 |
| 6,826,843 | B2 | 12/2004 | Lam et al. | |
| 7,041,910 | B2 | 5/2006 | Swager et al. | |
| 7,208,122 | B2 * | 4/2007 | Swager et al. | 422/82.05 |
| 7,214,543 | B2 | 5/2007 | Schanze et al. | |
| 7,326,908 | B2 | 2/2008 | Sargent et al. | |
| 7,718,130 | B1 * | 5/2010 | Shinar et al. | 422/82.07 |
| 2005/0147534 | A1 | 7/2005 | Swager et al. | |
| 2005/0196775 | A1 * | 9/2005 | Swager et al. | 435/6 |
| 2006/0051872 | A1 * | 3/2006 | Sailor et al. | 436/86 |
| 2006/0073607 | A1 | 4/2006 | Rose et al. | |
| 2007/0111321 | A1 | 5/2007 | Dean et al. | |
| 2007/0117954 | A1 | 5/2007 | Swager et al. | |
| 2007/0258864 | A1 | 11/2007 | Braymer et al. | |
| 2008/0248578 | A1 | 10/2008 | Dean et al. | |
| 2009/0066223 | A1 * | 3/2009 | Yabe et al. | 313/504 |
| 2009/0215189 | A1 | 8/2009 | Swager et al. | |
| 2009/0246881 | A1 * | 10/2009 | Toal et al. | 436/110 |
| 2009/0324446 | A1 | 12/2009 | Schanze et al. | |
| 2010/0022011 | A1 | 1/2010 | Swager et al. | |
| 2010/0112715 | A1 * | 5/2010 | Swager et al. | 436/110 |
| 2010/0173420 | A1 * | 7/2010 | Trogler et al. | 436/106 |
| 2011/0057116 | A1 * | 3/2011 | Trogler et al. | 250/458.1 |

OTHER PUBLICATIONS

Zhou, Q. et al, Journal of the American Chemical Society 1995, 117, 7017-7018.*
Zhou, Q. et al, Journal of the American Chemical Society 1995, 117, 12593-12602.*
Weder, C. et al, JOurnal of Physical Chemistry 1996, 100, 18931-18936.*
Harrison, M. G. et al, Physical Review B 1997, 55, 7831-7849.*
Lux, A. et al, Synthetic Metals 1997, 84, 293-294.*
Gurge, R. M. et al, Macromolecules 1997, 30, 8286-8292.*
Brandon, K. L. et al, Synthetic Metals 1997, 91, 305-306.*
Kunugi, Y. et al, Journal of the American Chemical Society 1998, 120, 589-590.*
Yang, J.-S. et al, et al, Journal of the American Chemical Society 1998, 120, 5321-5322.*
Kunigi, Y. et al, Chemistry of Materials 1998, 10, 1487-1489.*
Chen, S.-A. et al, Macromolecules 1998, 31, 4899-4907.*
Yang, J.-S. et al, et al, Journal of the American Chemical Society 1998, 120, 11864-11873.*
Nguyen, T.-Q. et al, Science 2000, 288, 652-656.*
Ajayaghosh, A. et al, Journal of the American Chemical Society 2001, 123, 5148-5149.*
Cassano, T. et al, Chemical Physics 2001, 272, 111-118.*
Burrows, H. D. et al, Chemical Physics 2002, 285, 3-11.*
Chang, C.-P. et al, Synthetic Metals 2004, 114, 297-301.*
George, S. J. et al, Chemistry—A European Journal 2005, 11, 3217-3227.*
Lynch, P. et al, SPIE 2005, 5826, 242-252.*
Toal, S. J. et al, Journal of Materials Chemistry 2006, 16, 2871-2883.*
Ajayaghosh, A. et al, Accounts of Chemical Research 2007, 40, 644-656.*
Cai, Y. et al, Sensors and Actuators B: Chemical 2008, 134, 727-735.*
Chen, H.-C. et al, Macromolecular Chemistry and Physics 2009, 210, 918-925.*
Caron, T. et al, Talanta 2010, 81, 543-548.*
Woodka, M, D, Analytical Chemistry 2010, 82, 9917-9924.*

* cited by examiner

*Primary Examiner* — Arlen Soderquist
(74) *Attorney, Agent, or Firm* — Richard J. Kim

(57) ABSTRACT

A senor uses a transduction mechanism of attenuating electroluminescence. Luminescence from a light emitting diode is attenuated as a consequence of direct interaction of an analyte and a electroluminescent material, An electroluminescent diode sensor (EDS) is fabricated in a way that allows the electroluminescent material in the diode to be exposed to gaseous, liquid or solid sample(s) which may affect the luminescence intensity of the diode.

15 Claims, 3 Drawing Sheets

ELECTROLUMINESCENT DIODE SENSOR

GOVERNMENT INTEREST

The invention described herein may be manufactured, used, sold, imported, and/or licensed by or for the Government of the United States of America.

FIELD OF THE INVENTION

This invention relates in general to sensing elements used in a sensor system, and more specifically to electroluminescent diode sensors.

BACKGROUND OF THE INVENTION

An electroluminescent diode sensor (EDS) can be used as a sensor. When energy is absorbed by a π-conjugated polymer, electrons are promoted from the highest occupied molecular orbital (HOMO) to the lowest unoccupied molecular orbital (LUMO) creating an excited state. The excited electron can relax down to the HOMO releasing a photon which is called a radiative process. Or the electron can relax down to the HOMO by a process that does not emit light, a non-radiative process.

SUMMARY OF THE INVENTION

A class of compounds that have the chemical characteristics to participate in the electron transfer reaction are nitroaromatic compounds. Nitroaromatic compounds include the explosives 2,4,6, trinitrotoluene (TNT) and dinitrotoluene (DNT) which make an electroluminescent diode sensor (EDS) a useful tool for sensing these explosive compounds. EDS can respond to chemicals that have such characteristics which could make it useful as a sensor, even for chemicals other than nitroaromatics, In one aspect, an electroluminescent sensor system is disclosed. An exemplary electroluminescent sensor system comprises an electroluminescent diode sensing element, wherein said electroluminescent diode sensing element emits electroluminescent light proximate to a sample of explosive compound; photodetector configured to detect electroluminescent light resulting from said electroluminescent diode sensing element proximate to a sample of explosive compound, and output a detection signal; a computer to process a detection signal from said photodetector; and a power supply to power at least said electroluminescent diode sensing element. Said detector detects electroluminescent light resulting from said electroluminescent diode sensing element proximate to a sample of explosive compound for said computer to process said detection signal and determine the presence of nitroaromatic molecules from any one of gaseous, liquid or solid samples which may affect the luminescence intensity of the electroluminescent diode sensing element.

In another aspect, a method of sensing molecules from an explosive sample is disclosed. An exemplary method can be based on a configured electroluminescent diode sensor, the method comprising applying a voltage from a power supply to the electroluminescent diode sensor to generate a radiation; detecting said radiation by a photodetector fur recording of the photodetector signal as a function of time by a computer; and processing said photodetector signal by the computer to monitor said photodetector signal and determine whether there has been an attenuation in an emitted light intensity sufficient to indicate the presence of nitroaromatic explosive molecules from any one of gaseous, liquid or solid samples which may affect the luminescence intensity of the diode sensor.

Yet, in another aspect, an electroluminescent diode sensor device is disclosed. An exemplary diode sensor device comprises a clear polyethylene terephthalate substrate; an indium tin oxide layer coating on said substrate; a poly(3,4-ethylenedioythiophene)/poly(styrene sulfonate) layer; a semiconducting polymer layer; an aluminum layer; a cathode connection to a power supply; and an anode connection to said power supply. A single layer of material of said electroluminescent diode sensor can serve as a radiation emitter and as a sensing material.

BRIEF DESCRIPTION OF THE DRAWINGS

Additional advantages and features will become apparent as the subject invention becomes better understood by reference to the following detailed description when considered in conjunction with the accompanying drawings. The detailed description is provided in reference to the attached drawings wherein.

DETAILED DESCRIPTION

The detailed description of the various exemplary embodiments of the present disclosure can be better understood from the following disclosure.

An electroluminescent diode sensor (EDS) can be configured as an explosive sensor device. An EDS can be configured as a sensor device to receive an electrical current applied to excite electrons in a π-conjugated polymer into an excited state. In an unperturbed system the EDS device emits light, When a molecule that has the proper redox potential and chemical properties comes in contact with the polymer in its excited state an electron transfer reaction happens causing the excited electrons to decay in a non-radiative process. This leads to a reduction in the amount of light that the sensor is generating.

A class of compounds that have the chemical characteristics to participate in the electron transfer reaction are nitroaromatic compounds. Nitroaromatic compounds include the explosives 2,4,6, trinitrotoluene (TNT) and dinitrotoluene (DNT) which make the EDS a useful tool for sensing these explosive compounds. Additionally, such an exemplary EDS device can show a response to any chemicals that have the characteristics which could make it useful as a sensor device, even for compounds other than nitroaromatics.

An electroluminescent diode sensor (EDS) can offer advantages when compared to other emission attenuation type explosive sensors. Advantages can be realized in the size of the sensor and the amount of information that can be obtained from its use.

For example, by exciting the sensing material electrically instead of optically the number of components in the sensor can be reduced. A reduced number of components can lead to a smaller and less complex sensor.

Second, an array of EDS can be formed using structurally different sensing materials on a chemical level. Varying responses from the different sensors can be used to mimic olfaction. Third, an emission spectrum of an EDS can be monitored and perturbations across it can be used to extract information about the attenuation species.

Figure 1:
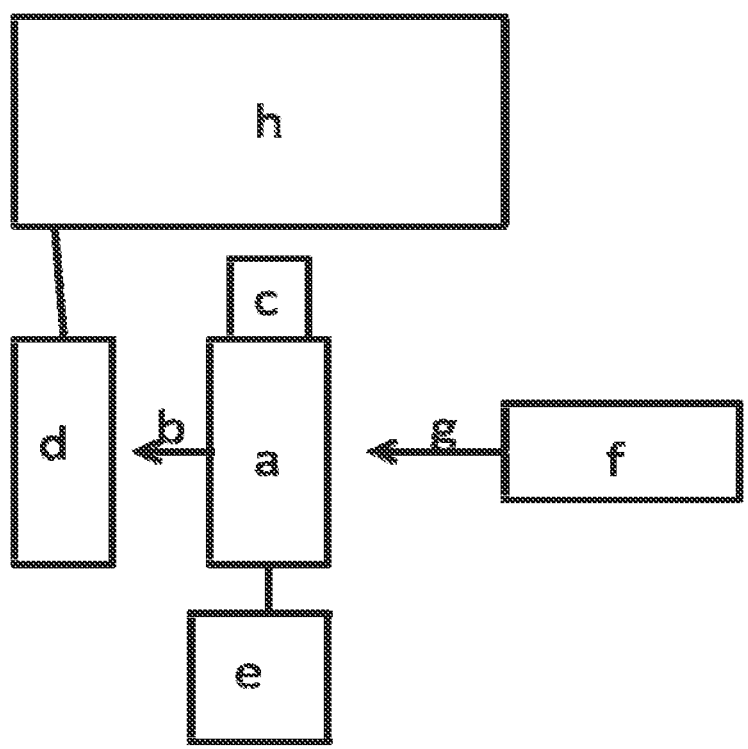
FIG. 1 shows an exemplary representation of a computer controlled electroluminescent diode sensor (EDS) configured with a photodetector to detect a sample nitroaromatic-explosive (e.g., trinitrotoluene) based TNT molecules.

SENSOR SYSTEM: Referring now to FIG. 1, FIG. 1 shows an exemplary embodiment of an Organic Light Emitting Diode (OLED) configured as a sensing element in a sensor system. As exemplified, FIG. 1 shows an exemplary configuration of said sensor system showing: a: electroluminescent diode sensor (EDS), b: light generated by the EDS, c: heater, d: photodetector, e: power supply, f: nitroaromatic explosive (e.g., trinitrotoluene), g: TNT molecules, and h: computer.

As exemplified, such a configured sensor system can function in this manner: The power supply (e) applies a voltage to the electroluminescent diode sensor (EDS) (a) causing it to generate radiation (b). The radiation is monitored by a photodetector (d) and a plot of the photodetector signal is recorded as a function of time on the computer (h). The presence of a nitroaromatic-based explosive (e.g., TNT) (f) generates vapor phase TNT molecules (g) which migrate to the sensing face of the EDS. The EDS and the TNT molecules then participate in an electron transfer reaction causing the amount of light generated by the EDS to decrease. When the computer monitors EDS signal vs. time, attenuations in emitted light intensity indicate the presence of nitroaromatic explosive molecules (e.g., TNT). A heater (c) provides heat to the EDS device which increases the kinetics of TNT adsorption and desorption onto the sensing face of the EDS.

SENSING METHOD: In another aspect, a method for electroluminescent diode sensing is disclosed, Method: Such an exemplary EDS can be used to effect an electron transfer reaction between a nitroaromatic compound and a semiconducting polymer in an excited state due to the direct injection of an electron from an electrode. This reaction is used as the transduction mechanism for an explosive sensor. The two reactants in this reaction are an electron withdrawing compound (trinitrotoluene) and a semiconducting polymer (poly [2,5-bisoctyl]-1,4 phenylenevinylene) in an excited state resulting from direct injection of an electron from a metallic cathode (Aluminum). The reaction is monitored by the change in radiation emitted from the polymer.

Figure 2A:
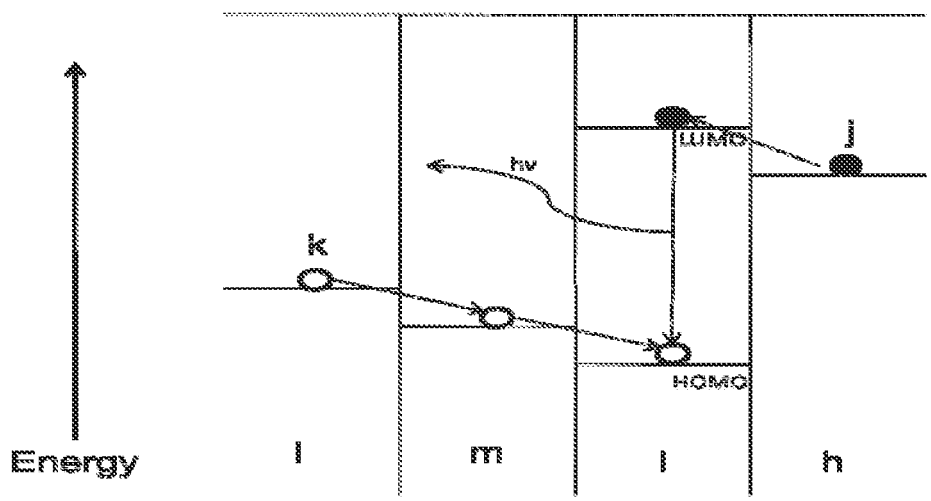
FIG. 2a shows an exemplary energy level diagram segmented by: h: Aluminum, i: poly[2,5-bisoctyl)-1,4 phenylenevinylene j: electrons, k: holes, l: Indium tin oxide anode, m: Poly(3,4-ethylenedioythiophene)/poly(styrene sulfonate).
Figure 2B:
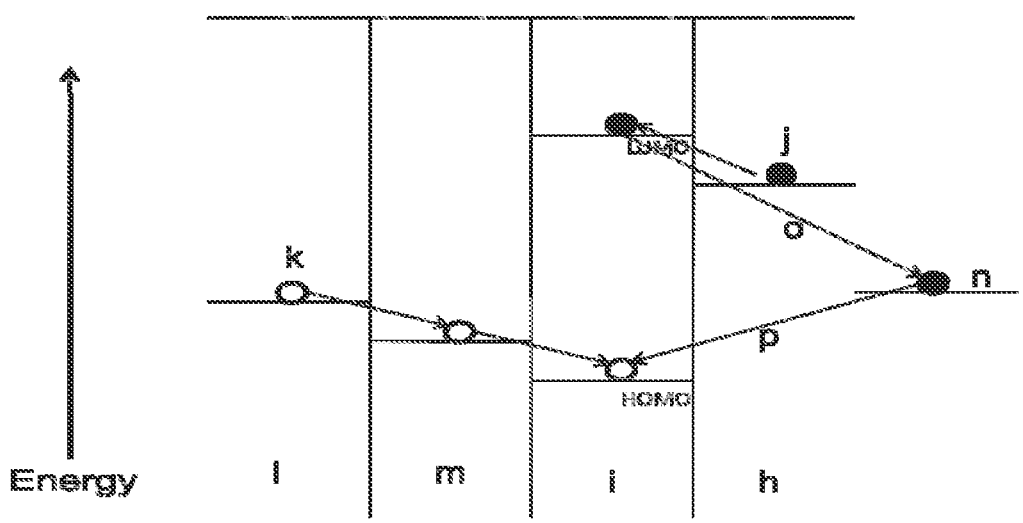
FIG. 2b shows an exemplary energy level diagram segmented by: h: Aluminum, i: poly[2,5-bisoctyl)-1,4 phenylenevinylene, j: electrons, k: holes, l: Indium tin oxide anode, m: Poly(3,4-ethylenedioythiophene)/poly(styrene sulfonate) n: trinitrotoluene, o: electron transfer from LUMO of i to n, p: electron transfer from n to HOMO of i.

An exemplary reaction method as follows and is described in the energy level diagrams FIGS. 2a and 2b. For example, FIG. 2a shows an exemplary energy level diagram segmented by: h: aluminum, i: poly[2,5-bisoctyl]-1,4 phenylenevinylene, j: electrons, k: holes, l: indium tin oxide anode, m: poly(3,4-ethylenedioythiaphene)/poly(styrene sulfonate).

In another aspect. FIG. 2b shows an exemplary energy level diagram segmented by: h: aluminum, i: poly[2,5-bisoctyl]-1,4 phenylenevinylene, j: electrons, k: holes, l: indium tin oxide anode, m: poly(3,4-ethylenedioythiophene)/poly(styrene sulfonate) n: trinitrotoluene, o: electron transfer from LUMO of i to n, p: electron transfer from n to HOMO of i.

To generate radiation (light) in the semiconducting polymer (Poly[2,5-bisoctyl)-1,4 phenylenevinylene) (i) has electrons (j) injected from a Aluminum cathode (h) into the lowest unoccupied molecular orbital (LUMO) of the polymer, holes (k) are injected from an Indium tin oxide anode (l) to a poly(3,4-ethylenedioythiophene)/poly(styrene sulfonate) hole injecting layer (m) to the highest occupied molecular orbital (HOMO) of the polymer (i). Electrons in the LUMO of the polymer fall into the holes in the HOMO of the polymer and the change in energy generates radiation (hv). This is how OLEDs function, and how the EDS functions under atmospheric conditions in the absence of nitroaromatic explosive.

The sensing reaction occurs when nitroaromatic explosives molecules (e.g., TNT) (n) come in contact with the polymer (i). The directly injected electron (j) is transferred (o) from the LUMO of the polymer to the trinitrotoluene and then back (p) to the HOMO of the polymer. The reaction is monitored by a computer controlled photodetector that displays a plot of intensity of radiation emitted by the semiconducting polymer versus time. Attenuations in the emitted radiation indicate occurrence of this electron transfer reaction and hence the presence of nitroaromatic explosives such as TNT.

Figure 3:
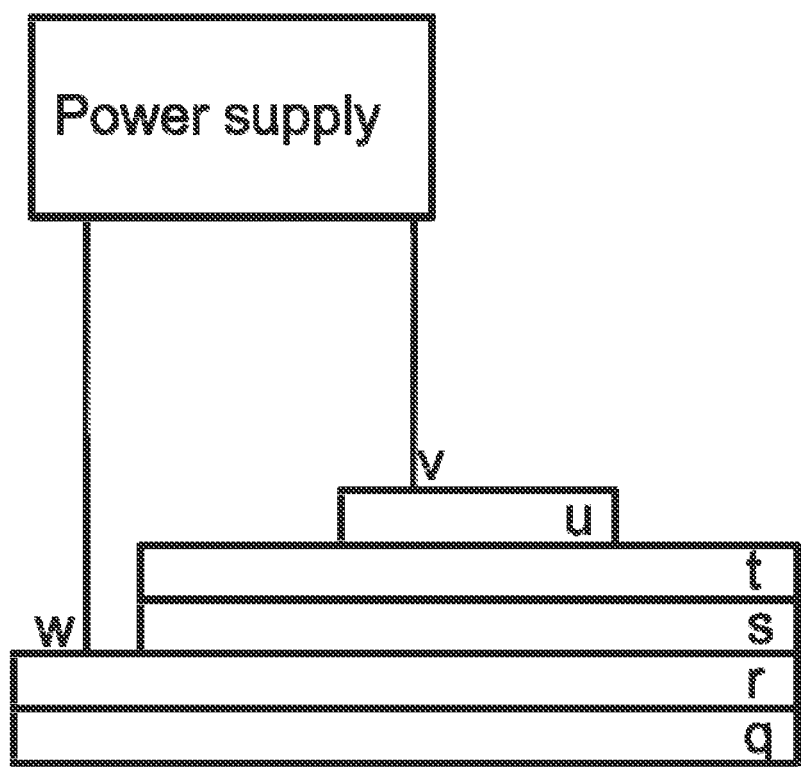
FIG. 3 shows an exemplary Electroluminescent Diode Sensor (EDS) configured based on: q: polyethylene terephthalate, r: Indium tin oxide, s: poly(3,4-ethylenedioythiophene)/poly(styrene sulfonate), t: poly[2,5-bisoctyl)-1,4 phenylenevinylene, u: aluminum, v: cathode connection, w: anode connection.

SENSOR DIODE: FIG. 3 shows an exemplary etectroluminescent diode sensor (EDS), wherein an exemplary EDS can be configured based on: q: polyethylene terephthalate, r: Indium tin oxide, s: poly(3,4-ethylenedioythiophene)/poly (styrene sulfonate), t: poly[2,5-bisoctyl]-1,4 phenylenevinylene, u: aluminum, v: cathode connection, w: anode connection. Such an exemplary electroluminescent diode sensor (EDS) can demonstrate the use of a single material as a radiation emitter and as a sensing material. As exemplified, such an EDS sensor diode can use a semiconducting polymer material poly[2,5-bisoctyl]-1,4 phenylenevinylene to generate radiation in an electroluminescent diode device while the same material is simultaneously used as a sensing material for nitroaromatic explosives, The EDS is constructed as seen in FIG. 3. On a clear polyethylene terephthalate (PET) (q) substrate coated with Indium tin oxide (ITO) (r) to 35Ω/cm surface resistivity a 40 nm thick layer of Poly(3,4-ethylenedioythiophene)/poly(styrene sulfonate) (PEDOT/PSS) (s) is coated and covered by a 150 nm thick layer of poly[2,5-bisoctyl]-1,4 phenyleneyinylene (t) on which a 200 nm thick layer of aluminum (u) is deposited.

ELECTROLUMINESCENT DETECTION: When electrical contacts are made on the aluminum (v) and ITO (w) surfaces an applied voltage of greater that 3V causes the poly[2,5-bisoctyl]-1,4 phenylenevinylene to emit radiation centered at 616 nm. This composite can also act as a sensing material by participating in an electron transfer reaction with electron withdrawing nitroaromatic explosive compounds such as trinitrotoluene.

Such an electron transfer reaction provides a pathway for non-radiative decay of the excited state electron. Thus decreases in the emitted radiation indicate the presence of reactive species such as trinitrotoluene.

It is obvious that many modifications and variations of the present invention are possible in light of the above teachings. It is therefore to be understood that within the scope of the appended claims, the invention may be practiced otherwise than as described.

What is claimed is:
1. An electroluminescent sensor system, comprising:
an electroluminescent diode sensing element, wherein said electroluminescent diode sensing element is configured with a heater and emits electroluminescent light proximate to a sample of explosive compound;

a photodetector configured to detect electroluminescent light resulting from said electroluminescent diode sensing element proximate to a sample of explosive compound, and output a detection signal;

a computer to process a detection signal from said photodetector; and a power supply to power at least said electroluminescent diode sensing element, wherein said detector detects electroluminescent light resulting from said electroluminescent diode sensing element proximate to a sample of explosive compound for said computer to process said detection signal and determine the presence of nitroaromatic molecules from any one of gaseous, liquid or solid samples which may affect the luminescence intensity of the electroluminescent diode sensing element.

2. The system recited in claim 1, wherein said electroluminescent diode sensing element comprises at least one of an electroluminescent diode sensor or an organic light emitting diode.

3. A method of sensing molecules from an explosive sample based on a configured electroluminescent diode sensor, the method comprising:

applying a voltage from a power supply to the electroluminescent diode sensor to generate a radiation, wherein heat from a heater is provided to the electroluminescent diode sensor to increase at least one of the kinetic adsorption and desorption onto a sensing face of the electroluminescent diode sensor;

detecting said radiation by a photodetector for recording of the photodetector signal as a function of time by a computer; and processing said photodetector signal by the computer to monitor said photodetector signal and determine whether there has been an attenuation in an emitted light intensity sufficient to indicate the presence of nitroaromatic explosive molecules from any one of gaseous, liquid or solid samples which may affect the luminescence intensity of the diode sensor.

4. The method recited in claim 3, wherein said nitroaromatic explosive molecules are from a TNT material.

5. The method recited in claim 3, wherein nitroaromatic explosive molecules are vapor-phase TNT molecules which migrate to a sensing face of the electroluminescent diode sensor, and wherein said electroluminescent diode sensor and the TNT molecules then participate in an electron transfer reaction causing the amount of light generated by the electroluminescent diode sensor to measurably decrease based on a recording or a plot of the photodetector signal as a function of time by the computer.

6. The method recited in claim 3, wherein said electroluminescent diode sensor and the TNT molecules then participate in an electron transfer reaction such that an electron transfer reaction between a nitroaromatic compound and a semiconducting polymer causes an excited state due to a direct injection of an electron from an electrode of the sensor, and wherein said reaction is used as the transduction mechanism for said electroluminescent diode sensor.

7. The method recited in claim 6, wherein two reactants in said reaction are an electron withdrawing compound such as trinitrotoluene and a semiconducting polymer (poly[2,5-bisoctyl)-1,4 phenylenevinylene) in an excited state resulting from direct injection of an electron from a metallic cathode such as Aluminum such that said reaction causes a measurable change in radiation emitted from the polymer.

8. The method recited in claim 3, wherein said radiation is generated in a semiconducting polymer of said electroluminescent diode sensor, wherein electrons are injected from a cathode of said electroluminescent diode sensor into a lowest unoccupied molecular orbital LUMO of the polymer, holes are injected from an indium tin oxide anode of said electroluminescent diode sensor to a hole injecting layer to the highest occupied molecular orbital HOMO of the polymer.

9. The method recited in claim 8, wherein electrons in the LUMO of the polymer fall into the holes in the HOMO of the polymer and the change in energy can generate radiation hv under atmospheric conditions in the absence of nitroaromatic explosive.

10. The method recited in claim 8, wherein a sensing reaction occurs when nitroaromatic explosives molecules come in contact with the polymer, and wherein a directly injected electron is transferred from the LUMO of the polymer to a trinitrotoluene and then back to the HOMO of the polymer.

11. The method recited in claim 10, wherein the sensing reaction is monitored by the computer controlled photodetector, capable of producing data for display or a plot of intensity of radiation emitted by the semiconducting polymer versus time.

12. The method recited in claim 3, wherein said attenuation in an emitted radiation can indicate an occurrence of an electron transfer reaction and hence the presence of nitroaromatic explosive molecules.

13. An electroluminescent diode sensor device, comprising:

a clear polyethylene terephthalate substrate;

an indium tin oxide layer coating on said substrate;

a poly(3,4-ethylenedioythiophene)/poly(styrene sulfonate) layer;

a semiconducting polymer layer;

an aluminum layer;

a cathode connection to a power supply; and an anode connection to said power supply, wherein a single layer of material of said electroluminescent diode sensor can serve as a radiation emitter and as a sensing material.

14. The sensor device recited in claim 13, wherein said semiconducting polymer layer uses a semiconducting polymer material poly[2,5-bisoctyl)-1,4phenylenevinylene about 150 nm thick layer to generate radiation in an electroluminescent diode device while the same material is simultaneously used as a sensing material for nitroaromatic explosives.

15. The sensor device recited in claim 13, wherein said clear polyethylene terephthalate substrate coated with indium tin oxide achieves 35 $\Omega$/cm surface resistivity, wherein said poly(3,4-ethylenedioythiophene)/poly(styrene sulfonate) layer is about 40 nm thick, and wherein said aluminum layer is about 200 nm thick.

* * * * *